(12) United States Patent
Plank et al.

(10) Patent No.: US 6,741,410 B2
(45) Date of Patent: May 25, 2004

(54) LIGHT RESOLUTION ELEMENT FOR IRRADIATING DENTAL REPLACEMENT PIECES WITH LIGHT TO EFFECT THE HARDENING THEREOF

(75) Inventors: Wolfgang Plank, Rankweil (AT); Thomas Stahl, Dauchingen (DE); Andreas Rathke, Schaan (LI)

(73) Assignee: Ivoclar Vivadent AG, Schaan (LI)

( * ) Notice: Subject to any disclaimer, the term of this patent is extended or adjusted under 35 U.S.C. 154(b) by 72 days.

(21) Appl. No.: 10/139,671

(22) Filed: May 6, 2002

(65) Prior Publication Data

US 2002/0171950 A1 Nov. 21, 2002

Related U.S. Application Data

(60) Provisional application No. 60/305,239, filed on Jul. 13, 2001.

(30) Foreign Application Priority Data

May 18, 2001 (DE) .......................... 101 24 367

(51) Int. Cl.⁷ .................. G02F 1/00; A61C 13/15; A61B 18/18
(52) U.S. Cl. ............... 359/834; 362/573; 362/581; 433/29; 606/14; 606/17
(58) Field of Search ............... 433/29, 30, 31; 362/572, 573, 581; 359/834; 606/13–19

(56) References Cited

U.S. PATENT DOCUMENTS

| 4,063,360 A | 12/1977 | Walker | |
| 4,468,197 A | * 8/1984 | Provost | 433/30 |
| 4,898,439 A | * 2/1990 | Mori | 385/31 |
| 5,030,093 A | * 7/1991 | Mitnick | 433/164 |
| 5,490,780 A | * 2/1996 | Riewenherm | 433/93 |
| 5,791,898 A | * 8/1998 | Maissami | 433/164 |
| 5,797,740 A | * 8/1998 | Lundvik | 433/29 |
| 5,800,163 A | 9/1998 | Rueggeberg et al. | |
| 6,280,187 B1 | * 8/2001 | Slone | 433/29 |
| 6,529,543 B1 | * 3/2003 | Anderson et al. | 372/108 |
| 2003/0021124 A1 | * 1/2003 | Elbrecht et al. | 362/572 |

FOREIGN PATENT DOCUMENTS

| DE | 295 11 927 U1 | 2/1997 |
| JP | 2000-316881 A | * 11/2000 |

* cited by examiner

Primary Examiner—John Juba, Jr.
(74) Attorney, Agent, or Firm—John C. Thompson; Alan S. Korman

(57) ABSTRACT

A light resolution element for a light guiding apparatus is provided that is connectable in optical communication with the light guiding apparatus for guiding and re-orienting light emitted thereto from the light guiding apparatus such that light exiting the light resolution element irradiates a dental restoration piece in a manner which effects complete hardening of the piece. The light resolution element includes a prismatic body operable to guide and re-orient a light beam passed thereto from the light guiding apparatus.

12 Claims, 2 Drawing Sheets

LIGHT RESOLUTION ELEMENT FOR IRRADIATING DENTAL REPLACEMENT PIECES WITH LIGHT TO EFFECT THE HARDENING THEREOF

CROSS-REFERENCE TO RELATED APPLICATIONS

This application claims foreign priority benefits under 35 U.S.C. §119(a)–(d) from German patent application ser. no. 101 24 367.7 filed May 18, 2001. In addition, this application claims the benefit under 35 U.S.C. §119(e) of U.S. provisional patent application ser. no. 60/305,239 filed Jul. 13, 2001.

BACKGROUND OF THE INVENTION

The present invention relates to a light resolution element for irradiating dental replacement pieces with light to effect the hardening of dental replacement pieces as well as a light hardening device having such a light resolution element.

It has long been known to use a light hardening device for hardening the dental replacement pieces in the mouths of dental patients. A representative approach is disclosed in U.S. Pat. No. 4,063,360. In this conventional solution, a light guiding apparatus guides ultraviolet light to the dental replacement piece and the polymerizable coating thereof is completely hardened by the ultraviolet light.

In order to ensure a satisfactory complete hardening of the corresponding coatings, it is necessary that ultraviolet light in sufficient quantities be guided to all of the regions of the dental replacement piece which are to be completely hardened.

In order to improve the true hardening of the dental replacement pieces, one strives to deliver the greatest possible light intensity in the given frequency range within which the plastic material that is to be hardened has the greatest sensitivity.

It has further been suggested to dispose the light emitting device as close as possible to the dental replacement part as well as to irradiate the dental replacement part from several positions. A solution in which the light source is disposed immediately bordering the dental replacement piece is disclosed in the embodiment shown in FIG. 2 of DE-GM 295 11 927. A solution in which the dental replacement piece is irradiated by light from several positions is described in U.S. Pat. No. 5,800,163.

On the other hand, it is desirable, at the least, to be able to subject those dental replacement pieces to a hardening process by a light emitting device wherein the diameter of the dental replacement piece is greater than approximately half the diameter of the light guiding apparatus. A solution according to U.S. Pat. No. 5,800,163 is not suitable for the treatment of such dental replacement parts and, instead, other types of light hardening devices must be deployed which are characterized in that they irradiate solely one side of the dental replacement piece. The known light hardening device is, at the same time, for all substantial purposes, only deployable for those dental replacement parts which project outwardly and cannot be deployed, in contrast, when inlays or onlays are involved.

SUMMARY OF THE INVENTION

The present invention offers a solution to the challenge of providing a light resolution element for a light guiding apparatus which can be deployed universally without having to anticipate disturbances in the handling of complex forms of the dental replacement pieces.

In accordance with the present invention, it is particularly advantageous that the light resolution element is configured as a prismatic body which extends in an obstacle free manner from the front and is not formed with any undercutting. Since the light irradiation path is provided within the prismatic body, disturbances of the light irradiation path by, for example, bridge elements, which would otherwise extend into the light beam path, are foreclosed. In one particular embodiment of the light resolution element of the present invention, the multiple re-orientation of the light beam path in the prismatic body permits a substantial enlargement of the acceptable diameter of the dental replacement piece which can be handled to include, for example, those pieces having a diameter which is substantially equal to the diameter of the light guiding apparatus as well as those pieces, as necessary, having a greater diameter.

In accordance with the present invention, these advantages are obtained by the configuration of a prismatic body having angled surfaces whereby an angled surface through which the light beam path first passes extends outwardly at, for example, an angle of 45°. In connection with the conventional configuration of prismatic bodies, due to the differing indexes of refraction between the body and air, the light beam path is reflected at the interface between the body and air at an angle of 90°—that is, radially toward the exterior.

In correspondence with the respective length to which the prismatic body extends toward the outside at that interface, there follows a shifting or offset of the light beams toward the outside, so that the strength of the prismatic body at this location determines the shift toward the outside.

Due to an outside oriented angled surface, whose angle corresponds to the angle of an interior angled surface, the light beam path is again re-oriented into an axis parallel direction. The light beam contacts, immediately before the point or apex of the light resolution element, a further angled surface which extends inwardly so that the light beam path is re-oriented radially toward the interior. The light beam path passes through a border surface between the prismatic body and air in a perpendicular direction so that the degree of reflection approaches zero thereat.

It is to be understood that, in accordance with a particular embodiment of the present invention, it can be provided that a body with a high light transmissivity is used as the prismatic body so that the light transmission losses through the light resolution element are, at most, only in the single digit percentage range. Additionally, in a further advantageous embodiment, it can be provided that the angled surfaces each mirror or reflect one another in order to approach a degree of reflection approaching 100%.

From the point of view of a further advantage of the present invention, the light resolution element is connected with the light guiding apparatus such that light is not inadvertently lost. In order to achieve this effect, it is provided that the light resolution element includes a bushing in which the end of the light guiding apparatus is tightly or tautly inserted. In an advantageous embodiment of the present invention, the diameter of the bushing is, in fact, somewhat smaller than the diameter of the end of the light guiding apparatus. The insertion of the light guiding apparatus is facilitated by insertion guiding surfaces and the light resolution element is seated under tension firmly on the light guiding apparatus.

Due to the firm seating between the light resolution element and the light guiding apparatus, the optical orientation of the light beam is additionally assured in the desired manner so that a loss of the light performance need not be feared.

It is to be understood that the firm connection of the light resolution element to the light guiding apparatus can be secured in any desired manner. Thus, for example, it is possible to provide a bayonet connection which secures the light resolution element to the light guiding apparatus.

As required, different elements can be made available, each of which is configured in correspondence with the type of light which will irradiate the dental replacement piece to effect polymerization thereof. The varying lengths of the angled surfaces permit flexible adjustment of the size of the light outlet region at the apex or peak of the light resolution element.

In accordance with a further modified embodiment of the present invention, it is provided that at least a third reflection surface in the front end of the light resolution element is convexly curved. In this connection, it is possible to focus the emitted light in a still stronger manner onto the dental replacement part in order to thereby make possible an improved light output.

In accordance with the present invention, it is particularly advantageous that the light resolution element handles a substantial portion of the light beam emitted from the light guiding apparatus and transfers the light beam to the dental restoration piece and, especially, that the light resolution element of the present invention can also be used, if desired, to perform a light hardening process in the mouth of the dental patient.

In accordance with the present invention, a type of channel extends between the shanks of the U-shaped element which permits a free positioning of the light resolution element.

BRIEF DESCRIPTION OF THE DRAWINGS

Additional advantages, details, and features are given in the hereinafter following description of an embodiment of the present invention taken in connection with the figures of the schematic drawings, in which.

DETAILED DESCRIPTION OF THE PREFERRED EMBODIMENT

Figure 1:
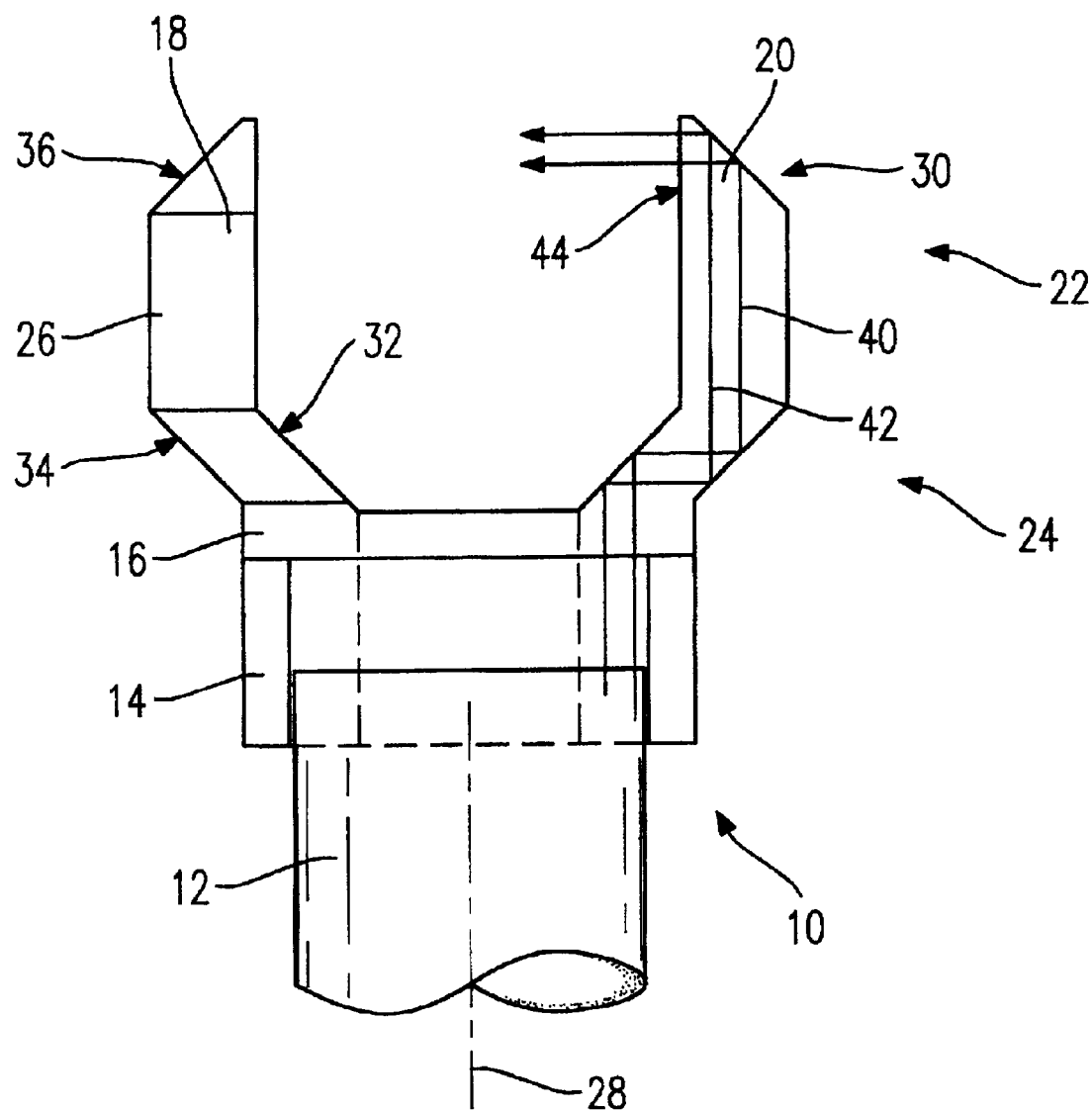
FIG. 1 is a front elevational view of one embodiment of the light resolution element of the present invention and shows the light resolution element in the disposition in which a light guiding apparatus has been inserted thereinto.

One embodiment of the light resolution element of the present invention is shown in FIG. 1 and is designated as the light resolution element 10. The light resolution element is shown in a disposition in which a light guiding apparatus 12 has been inserted thereinto and is, preferably, comprised of a transparent plastic. The light guiding apparatus is, in this configuration, configured as a light guide which guides light from a light source in a light loss-minimizing manner to the area of the mouth of a dental patient. A bushing 14 is provided as a component of the light resolution element 10 for connecting the light resolution element 10 to the light guiding apparatus 12, the inner diameter of the bushing 14 being compatibly dimensioned with respect to the outer diameter of the light guiding apparatus 12. The light resolution element is comprised of a light transmissive or light passing plastic such as polycarbonate. The elasticity of the material is sufficient to ensure a firm seating of the bushing 14 on the light guiding apparatus 12. Although FIG. 1 shows a disposition in which the light guiding apparatus 12 has not been completely inserted into the bushing 14, it is to be understood that, as needed, a full or complete insertion of the light guiding apparatus into the bushing can also be effected.

Light guiding components frequently exhibit the highest light intensity on their outer circumference. The light beams or radiation available thereat are, in accordance with the present invention, captured by the light resolution element of the present invention. The light resolution element includes a partition or distribution area 16 from which extend two shanks 18 and 20. The distribution area 16 is, in any event, preferably formed of transparent plastic and is seated in the manner of a cover over the bushing 14. The space comprised by the bushing 14 and the distribution area 16 is thus in the form of a cylindrical portion having a closure cover. The forward or front region of the light resolution element 10 is substantially U-shaped.

While in the illustrated embodiment of the light resolution element the distribution area 16 is configured as a short cylindrical body, it is to be understood that, as required, a light guiding configuration and a light beam re-orienting configuration can also be provided thereat such that a uniform light distribution or splitting is effected on the outlet side of the light guiding apparatus 12.

The shanks 18 and 20 form, in the forward region 22 of the light resolution element 10, a substantially U-shaped configuration. Each shank is configured in a particular configuration which is hereinafter described in more detail.

The shank 18 extends from the distribution area 16 initially at an angle of 45° outwardly. The partition area forms thereat, to this extent, an expansion or widening area 24.

The shank 18 extends thereafter in an axis parallel region 26 which is substantially parallel to the optical axis 28 of the light guiding apparatus. A re-orientation area 30 is provided at the forward or front end of the light resolution element 10 which re-orients the light beam path radially toward the interior.

The expansion or widening area 24 includes a first angled surface 32 in order to permit an expansion or broadening of the light beam. The angled surface 32 extends at an angle of 45° from the interior side of the shank 18 toward the outside. On a side of the light resolution element 10 opposite to the angled surface 32 there is formed a second angled surface 34 which extends parallel to the angled surface 32.

The re-orientation region 30 includes, in any event, a third angled surface 36.

The shank 20 is configured as a mirror image of the shank 18 so that the corresponding angled surfaces of the shank 20 are laid out or configured in an identical manner to those of the shank 18.

The light path 40 of a light beam emitted on the outer edge of the light guiding apparatus is representatively shown in FIG. 1 as well as a light beam path 42 of a further emitted light beam lying somewhat more in the middle of the light guiding apparatus. It can be seen that the three-fold re-oriented light beam path 40 as well as the light beam path 42 pass through an outlet surface 44 of the prismatic body in a substantially perpendicular orientation relative to the length extent of the light resolution element 10 in the direction of the shanks 18 and 20. The light beam path 40 and the light beam path 42 extend correspondingly radially toward the interior and irradiate the dental restoration piece which is disposed interiorly of the light resolution element 10. The light resolution element includes a polished over surface. The effect of a polished over surface is well known per se and is just an advantageous development of the invention.

Figure 2:
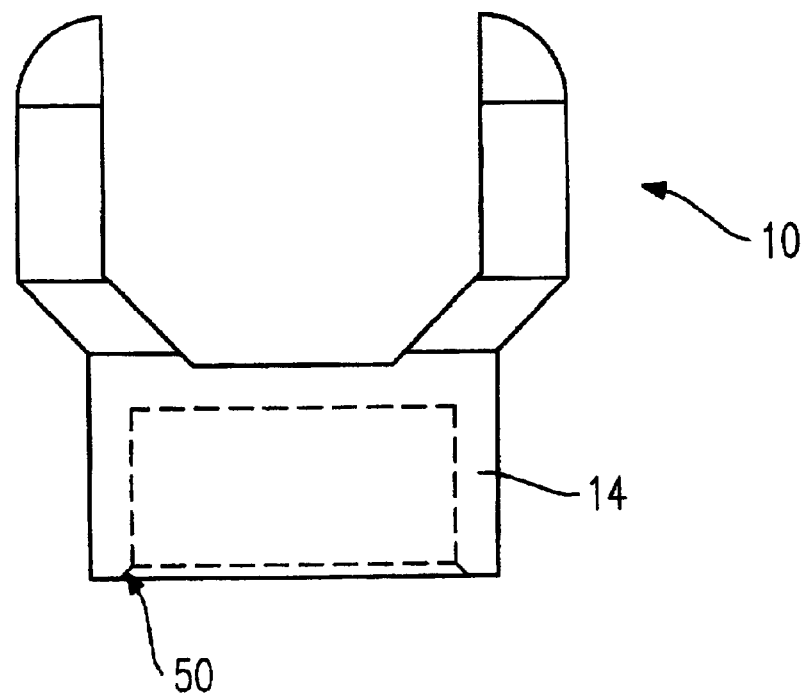
FIG. 2 is a side elevational view of the light resolution element shown in FIG. 1.

FIG. 2 shows the light resolution element 10 shown in FIG. 1 in a somewhat more simplified view without the light guiding apparatus 12. It can be seen that an insertion guide angle 50 is provided on the bottom inner edge of the bushing 14, extending at an angle of approximately 45°, which facilitates the insertion of the light guiding apparatus 12 into the bushing, if the diameter of the light guiding apparatus 12 corresponds to the inner diameter of the bushing 14.

Figure 3:
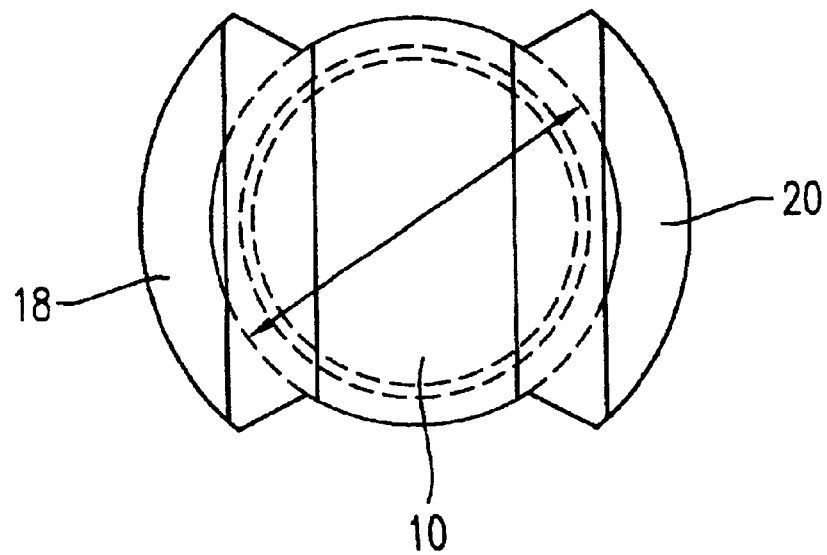
FIG. 3 is a top plan view of the light resolution element shown in FIGS. 1 and 2.

It can be seen in FIG. 3 that the shanks 18 and 20 of the light resolution element 10 extend over a substantial angled area of the light resolution element 10. In total, clearly more than half of the light beams of the light guiding apparatus cross-section, which exit therefrom in an annular area, are captured by the light resolution element 10 and guided to the shanks 18 and 20.

It is to be understood that an accommodation of the exact form of the angled surfaces can be made in connection with the requirements of the task. For example, the angled surfaces 32, 34, 36 can, as viewed in a top view, be curved or can extend in a straight orientation, all in accordance with whether or not an additional focusing is desired. Also, the angled surface 36 can be configured to be somewhat curved, as is shown in FIG. 2, so that an additional focusing follows.

The present invention is, of course, in no way restricted to the specific disclosure of the specification and drawings, but also encompasses any modifications within the scope of the appended claims.

What is claimed is:

1. A light resolution element (10) for a light guiding apparatus (12), which element is connectable in optical communication with the light guiding apparatus and by means of which light emitted thereto from the light guiding apparatus is re-orientable, with the light resolution element having an optical axis (28) and comprising:
   a prismatic body with prismatic angled surfaces (32, 34, 36) operable to guide and re-orient a light beam passed thereto from the light guiding apparatus, with the light resolution element being substantially U-shaped with a front region thereof facing away from the light guiding apparatus comprising two side shanks (18, 20) spaced from each other and extending substantially parallel to the optical axis of the light guiding apparatus and being part of the prismatic body.

2. A light resolution element according to claim 1, wherein the light guiding apparatus is configured as a light guide onto which the light resolution element is seated.

3. A light resolution element according to claim 1, wherein the U-shaped element have light outlet surfaces (44) in the two side shanks, said light outlet surfaces being for emitting light, said light being guided substantially perpendicular to the optical axis of the light guiding apparatus.

4. A light resolution element according to claim 1, wherein the light outlet surfaces extend substantially parallel to the optical axis of the light guiding apparatus.

5. A light resolution element according to claim 1, wherein the light resolution element includes a toward region having a light beam width which substantially corresponds to the thickness of the light guiding apparatus.

6. A light resolution element according to claim 1, further characterized by the provision of a light channel which extends in a substantially annular shape, and the side shanks extend from the light channel.

7. A light resolution element according to claim 1, wherein the light resolution element includes a first reflection surface which extends outwardly at an angle of approximately 45 and which reflects light outwardly in a direction substantially perpendicular to the longitudinal extent of the light guiding apparatus.

8. A light resolution element according to claim 7, wherein the light resolution element includes a second reflection surface which extends parallel to the first reflection surface and which re-orients light arriving thereat along outwardly extending perpendicular paths into paths which are substantially parallel to the longitudinal extent of the light guiding apparatus.

9. A light resolution element according so claim 8, wherein the light resolution element includes a third reflection surface (36) which extends from the first and second reflection surfaces and which re-orients light passing thereonto into paths toward the interior which are substantially perpendicular to the longitudinal extent of the light guiding apparatus.

10. A light resolution element according to claim 1, wherein the light resolution element includes side shanks which extend over an angle in the range of at least 45°.

11. A light resolution element according to claim 1, wherein the light resolution element is comprised of a polycarbonate plastic.

12. A light resolution element according to claim 1 wherein the light resolution element includes a polished over surface.

\* \* \* \* \*

UNITED STATES PATENT AND TRADEMARK OFFICE
CERTIFICATE OF CORRECTION

PATENT NO. : 6,741,410 B2
DATED : May 25, 2004
INVENTOR(S) : Wolfgang Plank et al.

It is certified that error appears in the above-identified patent and that said Letters Patent is hereby corrected as shown below:

<u>Column 6,</u>
Line 13, "toward" should be changed to -- forward --.
Line 33, "so" should be changed to -- to --.

Signed and Sealed this

Thirtieth Day of November, 2004

JON W. DUDAS
*Director of the United States Patent and Trademark Office*